US011065291B2

(12) United States Patent
Zuo et al.

(10) Patent No.: US 11,065,291 B2
(45) Date of Patent: Jul. 20, 2021

(54) TRADITIONAL CHINESE MEDICINE COMPOSITION FOR TREATING TUMOURS, PREPARATION METHOD THEREFOR AND USE THEREOF

(71) Applicants: Angang Zuo, Beijing (CN); Shixu Zuo, Beijing (CN); Na Zhao, Beijing (CN)

(72) Inventors: Angang Zuo, Beijing (CN); Shixu Zuo, Beijing (CN); Na Zhao, Beijing (CN)

(73) Assignees: Angang Zuo, Beijing (CN); Shixu Zuo, Beijing (CN); Na Zhao, Beijing (CN)

( * ) Notice: Subject to any disclaimer, the term of this patent is extended or adjusted under 35 U.S.C. 154(b) by 202 days.

(21) Appl. No.: 16/462,073

(22) PCT Filed: Sep. 11, 2017

(86) PCT No.: PCT/CN2017/101223
§ 371 (c)(1),
(2) Date: May 17, 2019

(87) PCT Pub. No.: WO2018/166151
PCT Pub. Date: Sep. 20, 2018

(65) Prior Publication Data
US 2019/0328813 A1 Oct. 31, 2019

(30) Foreign Application Priority Data

Mar. 13, 2017 (CN) .......................... 201710147162.1

(51) Int. Cl.
| A61K 36/481 | (2006.01) |
| A61P 35/00 | (2006.01) |
| A61K 36/074 | (2006.01) |
| A61K 36/236 | (2006.01) |
| A61K 36/284 | (2006.01) |
| A61K 36/285 | (2006.01) |
| A61K 36/287 | (2006.01) |
| A61K 36/355 | (2006.01) |
| A61K 36/484 | (2006.01) |
| A61K 36/534 | (2006.01) |
| A61K 36/54 | (2006.01) |
| A61K 36/61 | (2006.01) |

(52) U.S. Cl.
CPC .......... *A61K 36/481* (2013.01); *A61K 36/074* (2013.01); *A61K 36/236* (2013.01); *A61K 36/284* (2013.01); *A61K 36/285* (2013.01); *A61K 36/287* (2013.01); *A61K 36/355* (2013.01); *A61K 36/484* (2013.01); *A61K 36/534* (2013.01); *A61K 36/54* (2013.01); *A61K 36/61* (2013.01); *A61P 35/00* (2018.01)

(58) Field of Classification Search
None
See application file for complete search history.

(56) References Cited

U.S. PATENT DOCUMENTS 8,784,903 B2 * 7/2014 Park .................. A61P 17/18
424/725
2015/0283197 A1 10/2015 Xiao
2019/0328813 A1 10/2019 Zuo et al.

FOREIGN PATENT DOCUMENTS

| CN | 101612383 A | 12/2009 |
| CN | 101721619 A | 6/2010 |
| CN | 104013920 A | 9/2014 |
| CN | 104800459 A | 7/2015 |
| CN | 105265665 A | 1/2016 |
| CN | 106310120 A | 1/2017 |

OTHER PUBLICATIONS

Ling, Wenjing, Discussion on the Clinical Application and Law of Common Antitumor Traditional Chinese Medicine, Chinese Master's Theses Full-text Database, 2015, 96 pages.
Zhou, Caihong el al., Induced Cells Apoptosis by Cisplatin Combined with Chinese Medicine Jinan in Mice Lewis Lung Cancer, China Cancer, 12(3), 169-171, 2003.
Miu, Jianhua et al., Clove, Southern and Pan-southern Medicine, 2014, 4 pages.
Mei, Quanxi, Lonicera Japonica, Handbook of Pharmacology and Clinical Application of Modern Chinese Medicine 2016, 6 pages.
Jung Ha et al., Anti-tumorigenic Activity of Sophofavescenol Against Lewis Lung Carcinoma In Vitro and In Vivo, Archives of Pharmacal Research, 34(12): 2087-2099, 2011.
Seo DW et al., Phytochemical Linarin Enriched in the Flower of Chrysanthemum Indicum Inhibits Proliferation of A549 Human Alveolar Basal Epithelial Cells Through Suppression of the Akt-dependent Signaling Pathway, Journal of Medicinal Food, 16(12):1086-1094, 2013.
Lin L et al., Structural Elucidation of a Pectin from Flowers of Lonicera Japonica and its Antipancreatic Cancer Activity, International Journal of Biological Macromolecules, 88: 130-137, 2016.
Sharma V et al., In Vitro Anticancer Activity of Extracts of *Mentha* Spp. Against Human Cancer Cells, Indian Journal of Biochemistry & Biophysics, 51(5): 416-419, 2014.
Choi YH, Induction of Apoptosis by an Ethanol Extract of Poria Cocos Wolf. in Human Leukemia U937 Cells, Oncology Reports, 34(5): 2533-2540, 2015.
Xu J et al., Structural Characterization and Anti-tumor Effects of an Inulin-type Fructan from Atractylodes Chinensis, International Journal of Biological Macromolecules, 82: 765-771, 2016.

(Continued)

*Primary Examiner* — Susan Hoffman
(74) *Attorney, Agent, or Firm* — Metis IP LLC

(57) ABSTRACT

Disclosed are a traditional Chinese medicine composition for treating tumours and a preparation method therefor, wherein the composition is prepared from *Sophora flavescens*, wild *Chrysanthemum* flower, honeysuckle, mint, *Poria cocos*, *Atractylodes lancea*, cinnamon, clove, *Astragalus*, *Ganoderma lucidum*, *Ligusticum striatum*, *Aucklandia* root and *Radix glycyrrhizae*. The traditional Chinese medicine composition has an anti-tumour effect.

32 Claims, No Drawings

(56) References Cited

OTHER PUBLICATIONS

Kwom HK et al., Cinnamon Extract Induces Tumor Cell Death Through inhibition of NFkappaB and AP1, BMC Cancer, 2010, 10 pages.

Liu H et al., Clove Extract Inhibits Tumor Growth and Promotes Cell Cycle Arrest and Apoptosis, Oncology Research, 21(5): 247-259, 2014.

Jung Y et al., A Systematic Review of Anticancer Effects of Radix Astragali, Chinese Journal of Integrative Medicine, 22(3): 225-236, 2016.

Suarez-Arroyo IJ et al., Anti-tumor Effects of Ganoderma lucidurn (reishi) in Inflammatory Breast Cancer in In Vivo and In Vitro Models, PLoS ONE, 2013, 12 pages.

De La Cruz J et al., Anti Cancer Effects of Cnidium Officinale Makino Extract Mediated Through Apoptosis and Cell Cycle Arrest in the HT-29 Human Colorectal Cancer Cell Line, Asian Pacific Journal of Cancer Prevention, 15(13): 5117-5121, 2014.

Kumar A et al., UPLC/MS/MS Method for Quantification and Cytotoxic Activity of Sesquiterpene Lactones Isolated from Saussurea lappa, Journal of Ethnopharmacology, 155(2): 1393-1397, 2014.

Ji S et al., Bioactive Constituents of Glycyrrhiza Uralensis (Licorice): Discovery of the Effective Components of a Traditional Herbal Medicine, Journal of Natural Products, 79(2): 281-292, 2016.

Kyosuke Tsuda et al., Galenical Preparation, A Pharmaceutical Development Basic Course XI Pharmaceutical process (upper), 1971, 25 pages.

First Examination Report in Australian Application No. 2017403418 dated Mar. 13, 2020, 10 pages.

The Extended European Search Report in European Application No. 17900742.2 dated Nov. 2, 2020, 5 pages.

Notice of Reasons for Rejection in Japanese Application No. 2010547748 dated Jun. 23, 2020, 15 pages.

\* cited by examiner

TRADITIONAL CHINESE MEDICINE COMPOSITION FOR TREATING TUMOURS, PREPARATION METHOD THEREFOR AND USE THEREOF

FIELD OF THE DISCLOSURE

The present disclosure belongs to the field of traditional Chinese medicines, and relates to a traditional Chinese medicine composition for treating tumors, preparation method thereof and use thereof.

BACKGROUND OF THE DISCLOSURE

Currently, the treatment of the malignant tumors mainly adopts surgical treatment, chemotherapy or radiotherapy and so on, among them, surgical treatment has difficult postoperative recovery, and chemotherapy and radiotherapy have harmful side effects.

In the existing treatments of malignant tumors, the anti-tumor drug market has grown in recent years. Since tumor patients have increased year by year and most anti-tumor drugs have more toxic side effects, development of an anti-cancer drug with obvious effect and small side effects has an important implication.

SUMMARY OF THE DISCLOSURE

In one aspect, the present disclosure provides a traditional Chinese medicine composition for treating tumors. In another aspect, the present disclosure provides a preparation method of the traditional Chinese medicine composition for treating tumors. In further another aspect, the present disclosure provides a use of the traditional Chinese medicine composition for treating tumors and a method for treating tumors.

The traditional Chinese medicine composition for treating tumors of the present disclosure is prepared by raw materials with weight percentage as follows:

Sophora flavescens 3%-12%, wild Chrysanthemum flower 5%-15%, honeysuckle 2%-12%, mint 5%-15%, Poria cocos 5%-15%, Atractylodes lancea 10%-20%, cinnamon 0.5%-3%, clove 0.5%-3%, Astragalus 3%-12%, Ganoderma lucidum 5%-15%, Ligusticum striatum 10%-20%, Aucklandia root 5%-12%, and Radix glycyrrhizae 2%-10%.

In one embodiment, the traditional Chinese medicine composition for treating tumors is prepared by raw materials with weight percentage as follows:

Sophora flavescens 5%-10%, wild Chrysanthemum flower 5%-10%, honeysuckle 3%-8%, mint 5%-10%, Poria cocos 5%-10%, Atractylodes lancea 12%-20%, cinnamon 0.5%-3%, clove 0.5%-3%, Astragalus 5%-10%, Ganoderma lucidum 5%-10%, Ligusticum striatum 11%-15%, Aucklandia root 8%-12%, and Radix glycyrrhizae 3%-8%.

In one embodiment, the traditional Chinese medicine composition for treating tumors is prepared by raw materials with weight percentage as follows:

Sophora flavescens 6%-10%, wild Chrysanthemum flower 6%-9%, honeysuckle 3%-6%, mint 6%-9%, Poria cocos 6%-9%, Atractylodes lancea 15%-18%, cinnamon 1%-3%, clove 0.5%-1.5%, Astragalus 6%-10%, Ganoderma lucidum 6%-10%, Ligusticum striatum 12%-15%, Aucklandia root 8%-11%, and Radix glycyrrhizae 3%-6%.

In one embodiment, the traditional Chinese medicine composition for treating tumors is prepared by raw materials with weight percentage as follows:

Sophora flavescens 8%, wild Chrysanthemum flower 9%, honeysuckle 4%, mint 6%, Poria cocos 6%, Atractylodes lancea 17%, cinnamon 2%, clove 1%, Astragalus 8%, Ganoderma lucidum 10%, Ligusticum striatum 13%, Aucklandia root 9%, and Radix glycyrrhizae 7%.

In one embodiment, the traditional Chinese medicine composition for treating tumors is prepared by raw materials with weight percentage as follows:

Sophora flavescens 7%, wild Chrysanthemum flower 7%, honeysuckle 6%, mint 8%, Poria cocos 8%, Atractylodes lancea 15%, cinnamon 2%, clove 1.5%, Astragalus 7%, Ganoderma lucidum 8%, Ligusticum striatum 15%, Aucklandia root 10%, and Radix glycyrrhizae 5.5%.

In one embodiment, the traditional Chinese medicine composition for treating tumors is prepared by raw materials with weight percentage as follows:

Sophora flavescens 8%, wild Chrysanthemum flower 7%, honeysuckle 5%, mint 6%, Poria cocos 9%, Atractylodes lancea 18%, cinnamon 1.5%, clove 0.5%, Astragalus 6%, Ganoderma lucidum 9%, Ligusticum striatum 16%, Aucklandia root 9%, and Radix glycyrrhizae 5%.

In one embodiment, the traditional Chinese medicine composition for treating tumors is prepared by raw materials with weight percentage as follows:

Sophora flavescens 6%, wild Chrysanthemum flower 9%, honeysuckle 8%, mint 5%, Poria cocos 9%, Atractylodes lancea 19%, cinnamon 1%, clove 1%, Astragalus 6%, Ganoderma lucidum 15%, Ligusticum striatum 11%, Aucklandia root 9%, and Radix glycyrrhizae 10%.

In one embodiment, the traditional Chinese medicine composition for treating tumors is prepared by raw materials with weight percentage as follows:

Sophora flavescens 9%, wild Chrysanthemum flower 8%, honeysuckle 3%, mint 9%, Poria cocos 8%, Atractylodes lancea 16.5%, cinnamon 1%, clove 1%, Astragalus 9%, Ganoderma lucidum 9%, Ligusticum striatum 13.5%, Aucklandia root 10%, and Radix glycyrrhizae 3%.

In one embodiment, the dosage form of the traditional Chinese medicine composition for treating tumors is an injection, a honeyed pill, a water pill, a capsule, a tablet, a dripping pill, a powder, an oral solution, a gel, an electuary, an extract or a film.

In one aspect, the present disclosure provides the preparation method of the traditional Chinese medicine composition for treating tumors including the following steps:

Step (1), weighed the raw materials according to the weight percentage, crushed the raw materials and uniformly mixed after sieved.

Step (2), infiltrated the traditional Chinese medicine powder obtained from step (1) into ethanol, and poured into a percolator.

Step (3), poured ethanol into the percolator, and processing percolation after soak; prepared the drug residues obtained after percolation for later use, and obtained a traditional Chinese medicine compound powder A by concentrating and drying the obtained alcohol percolate.

Step (4), decocted the drug residues obtained from step (3) with water, filtrated, and obtained a traditional Chinese medicine compound powder B by concentrating and drying.

Step (5), uniformly mixed the traditional Chinese medicine compound powder A from step (3) and the traditional Chinese medicine compound powder B from step (4) to obtain the traditional Chinese medicine composition.

In one preferred embodiment, in step (1), the size of the crushed raw materials is 10-100 mesh, preferably 20-40 mesh, most preferably 24 mesh.

In another preferred embodiment, in step (2) and step (3), the concentration of ethanol is 40-95%, preferably 60-80%, most preferably 70%.

In another preferred embodiment, in step (2), the uniformly mixed traditional Chinese medicine powder was infiltrated for 10-48 hours, preferably for 18-30 hours, most preferably 24 hours.

In another preferred embodiment, in step (3), the soaking time is 2-48 hours, preferably 18-36 hours.

In another preferred embodiment, in step (4), the amount of water is 2-times of the drug residues, and the decoction is 1-3 times, each time for 0.5-2 hours.

In one embodiment, the preparation method of the traditional Chinese medicine composition for treating tumors including the following steps:

Step (1), weighed the raw materials according to the weight percentage, crushed the raw materials to 10-100 mesh and uniformly mixed after sieved.

Step (2), prepared a 40-95% ethanol; infiltrated the traditional Chinese medicine powder obtained from step (1) into the 40-95% ethanol for 10-48 hours, and poured into a percolator and gently paved.

Step (3), the prepared ethanol solution having a concentration of 40-95% is added into the percolator in the step (2) and added to the surface of the raw materials 1-2 cm. After soaking for a preset time, the remaining ethanol is percolation, and the drug residues are reserved, the obtained alcohol liquid is concentrated under pressure, and dried to obtain a traditional Chinese medicine compound powder A.

Step (4), added 2-10 times of the drug residues amount of water to the drug residues, decoction extracting for 0.5-2 hours, centrifuged and filtrated, and obtained a traditional Chinese medicine compound powder B by concentrated and dried under reduced pressure, and obtained the traditional Chinese medicine composition by uniformly mixing the traditional Chinese medicine compound powder A and the traditional Chinese medicine compound powder B.

In one preferred embodiment, in step (1), the size of the crushed raw materials is 20-40 mesh, most preferably 24 mesh; in step (2) and step (3), the concentration of ethanol is 60-80%, most preferably 70%.

In one preferred embodiment, in step (2), the uniformly mixed traditional Chinese medicine powder was infiltrated for 18-30 hours, most preferably 24 hours; and, in step (3), the soaking time is 2-48 hours, preferably 18-36 hours.

In one aspect, the present disclosure further provides the preparation method of the traditional Chinese medicine composition for treating tumors including the following steps:

Step (1), weighed *Ligusticum striatum, Atractylodes lancea, Aucklandia* root, clove, cinnamon, and mint according to the weight percentage, extracting volatile oil by water, and processed the extracted volatile oil with cyclodextrin to obtain a volatile oil cyclodextrin inclusion complex. After filtration, the water decoction, the collecting the filtrate and the drug residues were collected for later use.

Step (2), mixed the drug residues obtained from step (1) after extracting the volatile oil with weighed *Poria cocos, Astragalus,* wild *Chrysanthemum* flower, *Ganoderma lucidum*, honeysuckle, *Sophora flavescens*, and *Radix glycyrrhizae*, according to the weight percentage, decocting with water and then filtrating, and combining the filtrate of decoction with the filtrate obtained after extracting the volatile oil to obtain a traditional Chinese medicine mixed solution.

Step (3), concentrated the traditional Chinese medicine mixed solution to paste, precipitated with ethanol, and a traditional Chinese medicine mixed alcohol solution being obtained after filtration.

Step (4), after concentration and drying the traditional Chinese medicine mixed alcohol solution, added the volatile oil cyclodextrin inclusion complex, so as to obtain the traditional Chinese medicine composition.

In certain embodiments, the amount of water used in volatile oil extraction is 4-15 times than the medicine materials, preferably 4-8 times, most preferably 6 times, extraction time is 2-12 hours, and the volatile oil is processed with a cyclodextrin inclusion process under 40° C. for 1-10 hours, preferably 2-8 hours, most preferably 6 hours.

In certain embodiments, step (2) further includes mixing the drug residues obtained by extracting the volatile oil extraction with weighed *Poria cocos, Astragalus,* wild *Chrysanthemum* flower, *Ganoderma lucidum*, honeysuckle, *Sophora flavescens*, and *Radix glycyrrhizae*, according to the weight percentage, adding 10-15 times of the amount of water and decocting for 2-5 times, each times for 1-2 hours, and then filtrating, and mixing the filtrate of decoction and the filtrate obtained after extracting the volatile oil to obtain the traditional Chinese medicine mixed solution.

In certain embodiments, step (3) further includes concentrating the traditional Chinese medicine mixed solution from step (2) by water bath, concentrated to a relative density of 1.06-1.08 paste, adding ethanol to make the ethanol content up to 60%, standing still for 12-72 hours, and filtrating to obtain the traditional Chinese medicine mixed alcohol solution.

In certain embodiments, the preparation method of the traditional Chinese medicine composition for treating tumors including the following steps:

Step (1), weighed *Ligusticum striatum, Atractylodes lancea, Aucklandia* root, clove, cinnamon, and mint according to the weight percentage, extracted volatile oil by water, and processed the extracted volatile oil with cyclodextrin to obtain a volatile oil cyclodextrin inclusion complex, filtrating the water decoction and the collected the filtrate and the drug residues for later use.

Step (2), mixed the drug residues obtained by extracting the volatile oil with weighed *Poria cocos, Astragalus,* wild *Chrysanthemum* flower, *Ganoderma lucidum*, honeysuckle, *Sophora flavescens*, and *Radix glycyrrhizae*, according to the weight percentage, decocted with water and then filtrated, and combined the filtrate of decoction with the filtrate obtained after extracting the volatile oil to obtain a traditional Chinese medicine mixed solution.

Step (3), concentrated the traditional Chinese medicine mixed solution to paste by water bath, precipitating with ethanol, adding alcohol to make the ethanol content up to 50-80% and to obtain a traditional Chinese medicine mixed alcohol solution.

Step (4), concentrated the traditional Chinese medicine mixed alcohol solution under reduced pressure, after dried, and added the volatile oil cyclodextrin inclusion complex, so as to obtain the traditional Chinese medicine composition.

In certain embodiments, in step (1), the amount of water used in volatile oil extraction is 4-15 times than the medicine materials, and the volatile oil is processed with cyclodextrin under 40° C. for 1-10 hours.

In certain embodiments, step (2) further includes mixing the drug residues obtained by extracting the volatile oil extraction with weighed *Poria cocos, Astragalus,* wild *Chrysanthemum* flower, *Ganoderma lucidum*, honeysuckle,

*Sophora flavescens*, and *Radix glycyrrhizae*, according to the weight percentage, adding 10-15 times of the amount of water and decocting for 2-5 times, each times for 1-2 hours, and then filtrating, and mixing the filtrate of decoction and the filtrate obtained after extracting the volatile oil to obtain the traditional Chinese medicine mixed solution.

In certain embodiments, step (3) further includes concentrating the traditional Chinese medicine mixed solution from step (2) by water bath, concentrated to a relative density of 1.06-1.08 paste, adding ethanol to make the ethanol content up to 60%, standing still for 12 hours or more, and filtrating to obtain the traditional Chinese medicine mixed alcohol solution.

In certain embodiments, the preparation method of the traditional Chinese medicine composition for treating tumors including the following steps:

Step (1), weighed the raw materials according to the weight percentage, and mixing uniformly.

Step (2), added ethanol solution into the uniformly mixed raw materials from step (1), preferably 40-80% ethanol, heating and refluxing for 1-4 times, each time for 1-2 hours, merging the extracts, recovering the ethanol under reduced pressure, and concentrating and drying to obtain the traditional Chinese medicine composition.

In certain embodiments, in step (2), the concentration of ethanol is 50-70%, most preferably 60%.

In certain embodiments, the preparation method of the traditional Chinese medicine composition for treating tumors including the following steps:

Step (1), weighed the raw materials according to the weight percentage.

Step (2), prepared 40-80% ethanol for use, added the uniformly mixed traditional Chinese medicine into the he prepared ethanol solution, heating and refluxing for 1-4 times, each time for 1-2 hours, merging the extracts, recovering the ethanol under reduced pressure, and concentrating and drying to obtain the traditional Chinese medicine composition.

In certain embodiments, in step (2), the concentration of the prepared ethanol is 50-70%, most preferably 60%.

In one aspect, the present disclosure provides a use of the traditional Chinese medicine composition for treating tumors for the preparation of a medicament for treating tumors.

In one aspect, the present disclosure provides a method for treating tumor, and the traditional Chinese medicine composition for treating tumors of the present disclosure is administered to a subject in need thereof.

In one aspect, the present disclosure provides a traditional Chinese medicine composition for treating tumors for use in treating a tumor.

The main active ingredient of the traditional Chinese medicine composition is *Sophora flavescens*, providing with the effect of "bitter and cold", and "heat and dampness". The effect "bitter and cold" of *Sophora flavescens* can relive fever, reduce the diarrhea and clean up the muggy in body which caused by moist and hot weather. The secondary active ingredients are wild *Chrysanthemum* flower, honeysuckle, mint, *Poria cocos*, and *Atractylodes lancea*, which enhance the effect of "bitter and cold". Among them, wild *Chrysanthemum* flower, honeysuckle, and mint can eliminate cold and fever, so as to remove the heat-toxicity from the lung; *Poria cocos* and *Atractylodes lancea* provide with the effect can strengthen the spleen and remove dampness to clean up the damp in spleen and stomach. However, the "yang-qi" would weak while removing the damp heat, so that cinnamon and clove were added as heat supply to regulate the "bitter and cold" and to prevent the weaken "yang-qi". *Astragalus* and *Ganoderma lucidum* can boost "qi" and strengthen healthy energy to strengthen body resistance. In addition, the effect of "warming yang-qi" and strengthen healthy energy used together can prevent the harmful of spleen and stomach result from the excessive "bitter and cold". *Ligusticum striatum* and *Aucklandia* root can promote blood circulation and activate "qi", and thus the blocked dampness and the heat-toxicity can be removed via circulation. Therefore, cinnamon, clove, *Astragalus, Ganoderma lucidum, Ligusticum striatum*, and *Aucklandia* root are adjuvants. *Radix glycyrrhizae* was used for regulating ingredients and adjuvants, and has the effect of boosting "qi", consolidation of exterior and warming spleen and stomach.

The remarkable anti-tumor efficacy of the traditional Chinese medicine composition of the present disclosure was confirmed by the rat and mice model of pharmacodynamic test. The traditional Chinese medicine composition has the effect of enhancing the immune function and anti-tumor. In addition, the raw materials of the traditional Chinese medicine composition are easy to obtain, the preparation method is simple, and the cost is relatively low.

DETAILED DESCRIPTION OF THE EXEMPLARY EMBODIMENTS

First Embodiment

A traditional Chinese medicine composition for treating tumors including a material prepared by raw materials with weight percentage as follows:

*Sophora flavescens* 8%, wild *Chrysanthemum* flower 9%, honeysuckle 4%, mint 6%, *Poria cocos* 6%, *Atractylodes lancea* 17%, cinnamon 2%, clove 1%, *Astragalus* 8%, *Ganoderma lucidum* 10%, *Ligusticum striatum* 13%, *Aucklandia* root 9%, and *Radix glycyrrhizae* 7%.

The preparation method of the traditional Chinese medicine composition includes the following steps. According to the weight percentage described above, the weighed raw materials were crushed to particle size and uniformly mixed after sieved to 20 mesh. A 70% ethanol solution was prepared for later use. Infiltrated the uniformly mixed raw materials into the 70% ethanol solution for at least 24 hours, poured the mixture into a percolator, and then gently pave the mixture. The 70% ethanol solution was added into the percolator and higher than the surface of the raw materials 1-2 cm, soaking for 18-30 hours (optimally, for 20 hours). Percolated the ethanol and retain the drug residues for later use. The percolated ethanol was concentrated under reduced pressure and dried to obtain traditional Chinese medicine compound powder A. The drug residues were added into water which the amount was twice to 10 times (most preferably, 8 times) than the drug residues thereof, and decocted for 0.5-2 hours. After centrifugation and filtration, the drug solution was concentrated under reduced pressure and dried to obtain traditional Chinese medicine compound powder B. Uniformly mixed the traditional Chinese medicine compound powder A and the traditional Chinese medicine compound powder B to obtain the traditional Chinese medicine composition.

Second Embodiment

A traditional Chinese medicine composition for treating tumors including a material prepared by raw materials with weight percentage as follows:

*Sophora flavescens* 7%, wild *Chrysanthemum* flower 7%, honeysuckle 6%, mint 8%, *Poria cocos* 8%, *Atractylodes lancea* 15%, cinnamon 2%, clove 1.5%, *Astragalus* 7%, *Ganoderma lucidum* 8%, *Ligusticum striatum* 15%, *Aucklandia* root 10%, and *Radix glycyrrhizae* 5.5%.

The preparation method of the traditional Chinese medicine composition includes the following steps. Weighed *Ligusticum striatum, Atractylodes lancea, Aucklandia* root, clove, cinnamon, and mint according to the weight percentage, and added appropriate amount of extraction solvent to extract volatile oil, the extraction solvent is 6 times the amount of the medicinal materials, extract time is 2-20 hours (optimally 10 hours), and the volatile oil was processed with cyclodextrin under 40° C. to obtain a volatile oil cyclodextrin inclusion complex. The time of cyclodextrin inclusion process was 6 hours. The filtrate after the volatile oil extraction was collected for later use. The drug residues after the volatile oil extraction was mixed with weighed *Poria cocos, Astragalus*, wild *Chrysanthemum* flower, *Ganoderma lucidum*, honeysuckle, *Sophora flavescens*, and *Radix glycyrrhizae*, according to the weight percentage, and added into water which amount was 10-15 times (optimally, 12 times) than the drug residues and the medicinal materials thereof, and decocted for 2-5 times (optimally 3 times), and each time for 1-2 hours (optimally 1.5 hours). Filtered the decocted drug solution and mixed the drug solution with the filtrate after the volatile oil extraction to obtain a traditional Chinese medicine mixed solution. The traditional Chinese medicine mixed solution was concentrated by water bath and concentrated to the relative density of 1.06-1.08 paste, and then added ethanol containing alcohol amounted to 60%, stand still for 12 hours or more to obtain a traditional Chinese medicine mixed alcohol solution. The traditional Chinese medicine mixed alcohol solution was concentrated under reduced pressure, dried, and added with the volatile oil cyclodextrin inclusion complex, so as to obtain the traditional Chinese medicine composition.

Third Embodiment

A traditional Chinese medicine composition for treating tumors including a material prepared by raw materials with weight percentage as follows:

*Sophora flavescens* 8%, wild *Chrysanthemum* flower 7%, honeysuckle 5%, mint 6%, *Poria cocos* 9%, *Atractylodes lancea* 18%, cinnamon 1.5%, clove 0.5%, *Astragalus* 6%, *Ganoderma lucidum* 9%, *Ligusticum striatum* 16%, *Aucklandia* root 9%, and *Radix glycyrrhizae* 5%.

The preparation method of the traditional Chinese medicine composition includes the following steps. Weighed the raw materials according to the weight percentage described above. A 60% ethanol solution was prepared for later use. Soaked the uniformly mixed raw materials into the 60% ethanol solution, which was 6 times the amount of the raw materials thereof. The mixture was heated under reflux for 2 times (heated to lightly boiling for reflux extraction) for 1-2 hours (optimally 1.5 hours), and twice of the extracts were merged, and the ethanol was recovered under reduced pressure, followed by concentration and drying to obtain the traditional Chinese medicine composition.

Fourth Embodiment

A traditional Chinese medicine composition for treating tumors including a material prepared by raw materials with weight percentage as follows:

*Sophora flavescens* 6%, wild *Chrysanthemum* flower 9%, honeysuckle 8%, mint 5%, *Poria cocos* 9%, *Atractylodes lancea* 19%, cinnamon 1%, clove 1%, *Astragalus* 6%, *Ganoderma lucidum* 15%, *Ligusticum striatum* 11%, *Aucklandia* root 9%, and *Radix glycyrrhizae* 10%.

The preparation method of the traditional Chinese medicine composition includes the following steps. According to the weight percentage described above, the weighed raw materials were crushed to particle size and uniformly mixed after sieved to 30 mesh. A 65% ethanol solution was prepared for later use. Infiltrated the uniformly mixed raw materials into the 65% ethanol solution for 36 hours, poured the mixture into a percolator, and then gently pave the mixture. The 65% ethanol solution was added into the percolator and higher than the surface of the raw materials 1-2 cm, soaking for 18 hours. Percolated the ethanol and retain the drug residues for later use. The percolated ethanol was concentrated under reduced pressure and dried to obtain traditional Chinese medicine compound powder A. The drug residues were added into water which the amount was 5 times than the drug residues thereof and decocted for 1-2 hours (optimally 1.5 hours). After centrifugation and filtration, the drug solution was concentrated under reduced pressure and dried to obtain traditional Chinese medicine compound powder B. Uniformly mixed the traditional Chinese medicine compound powder A and the traditional Chinese medicine compound powder B to obtain the traditional Chinese medicine composition.

Fifth Embodiment

A traditional Chinese medicine composition for treating tumors including a material prepared by raw materials with weight percentage as follows:

*Sophora flavescens* 9%, wild *Chrysanthemum* flower 8%, honeysuckle 3%, mint 9%, *Poria cocos* 8%, *Atractylodes lancea* 16.5%, cinnamon 1%, clove 1%, *Astragalus* 9%, *Ganoderma lucidum* 9%, *Ligusticum striatum* 13.5%, *Aucklandia* root 10%, and *Radix glycyrrhizae* 3%.

The preparation method of the traditional Chinese medicine composition includes the following steps. Weighed *Ligusticum striatum, Atractylodes lancea, Aucklandia* root, clove, cinnamon, and mint according to the weight percentage, and added appropriate amount of extraction solvent to extract volatile oil, the extraction solvent is 4 times the amount of the medicinal materials, extract time is 2-12 hours (optimally 10 hours), and the volatile oil was processed with cyclodextrin under 40° C. to obtain a volatile oil cyclodextrin inclusion complex. The time of cyclodextrin inclusion process was 5 hours. The filtrate after the volatile oil extraction was collected for later use. The drug residues after the volatile oil extraction was mixed with weighed *Poria cocos, Astragalus*, wild *Chrysanthemum* flower, *Ganoderma lucidum*, honeysuckle, *Sophora flavescens*, and *Radix glycyrrhizae*, according to the weight percentage, and added into water which amount was 10-15 times (optimally, 12 times) than the drug residues and the medicinal materials thereof, and decocted for 2-5 times (optimally 3 times), and each time for 1-2 hours (optimally 1.5 hours). Filtered the decocted drug solution and mixed the drug solution with the filtrate after the volatile oil extraction to obtain a traditional Chinese medicine mixed solution. The traditional Chinese medicine mixed solution was concentrated by water bath and concentrated to the relative density of 1.06-1.08 paste, and then added ethanol containing alcohol amounted to 60%, stand still for 12 hours or more (optimally 24 hours) to obtain a traditional Chinese medicine mixed alcohol solution. The traditional Chinese medicine mixed alcohol solution was concentrated under reduced pressure, dried, and added with the volatile oil cyclodextrin inclusion complex, so as to obtain the traditional Chinese medicine composition.

Pharmacodynamic Test:

To examine the effect of the traditional Chinese medicine composition of the present disclosure in treating tumor, the traditional Chinese medicine composition respectively prepared by the first embodiment and the second embodiment (respectively referred to as traditional Chinese medicine composition No. 1 and traditional Chinese medicine composition No. 2) were used for the following pharmacodynamic test.

The clinical recommended dose for adult of the traditional Chinese medicine composition for treating tumor of the present disclosure is 7.6 g crude drug/60 kg/d, the equivalent dose of nude mouse is 1.4 g/kg/d. 2.8, 1.4, 0.7 g/kg/d three dose groups (respectively corresponding to twice, equivalent and ½ fold of the clinical dose for adult) were administered in the test.

Inhibition of the traditional Chinese medicine composition for treating tumor of the present disclosure on the human lung adenocarcinoma cell line (A549) in nude mice model.

Compared with the model group, the tumor volume of each dosage group obtained from embodiments 1 and 2 administration was decreased, and the tumor volumes of the groups of day 8 administration were significantly decreased (P<0.01, P<0.05). Compared with the model control group, the T/C % of the traditional Chinese medicine composition No. 1 with high dose group and the traditional Chinese medicine composition No. 2 with medium dose group were 28-70%. Each tumor weight of the administration groups had difference from the tumor weight of the model control group (P<0.01). These result shows that the tumor volume of the traditional Chinese medicine composition No. 2 with medium dose group at the 5 detection time from day 4 to 20 of administration were different (P<0.01) from the tumor volume of the model control group, the T/C % of the traditional Chinese medicine composition No. 2 with medium dose group was lower than 40% after the day 8 administration, and the traditional Chinese medicine composition No. 2 with medium dose group has the smallest tumor lump.

1 Test Material 1.1 Test drug: traditional Chinese medicine composition No. 1 and traditional Chinese medicine composition No. 2. Administration and dosage: oral, the clinical recommended dose is 7.6 g of crude drug daily.

1.2 Positive control drug: compound cyclophosphamide tablet, manufacturer: Tonghua Maoxiang Pharmaceutical Co., Ltd. Indications: malignant lymphoma, multiple myeloma, lymphocytic leukemia, neuroblastoma tumor, ovarian cancer, breast cancer and lung cancer, and various sarcomas. Lot number: 160702, manufacture date: 2016.07.25, expiry date: 2018.06. Ingredients: compound, component: cyclophosphamide (50 mg) and ginsenoside extract of Ginseng stems and leaves (50 mg). Properties: enteric coated tablets, appearing yellowish or taupe after removal of the coating. Specifications: cyclophosphamide 50 mg, ginsenoside extract of Ginseng stems and leaves 50 mg, 12 tablets/plate, 2 plates/box. Dosage of use: 1 tablet at a time, 3-4 times a day for adults. Storage conditions: shading, sealed and stored below 30° C.

1.3 Test animals

| Strain | Level | weight | numbers | gender | Certificate number | Certificate number | Provided by |
|---|---|---|---|---|---|---|---|
| nude mice, BALB/c Nude | SPF grade | 19 ± 1 g | 88 | male/female evenly | SCXK(Beijing)2012-0001 | 11400700187753 | Beijing Vital River Laboratory Animal Technology Co., Ltd |

1.4 Tumor cell line

| Tumor cell line | Use | Resource |
|---|---|---|
| A549 human lung adenocarcinoma cancer cell | establishing lung cancer xenograft model on nude mice | Cell Culture Center of Chinese Academy of Medical Sciences Basics Medical Science Institute |

2 Test Method 2.1 Dosage Design 2.1.1 The traditional Chinese medicine composition for treating tumor: the clinical recommended dose for adult is 7.6 g crude drug/60 kg/d. Converted according to the test body surface area in terms of human and animal, the dosage of mice is 11 times the dosage of human, and the administration dose of mice is (7.6/60)×11=1.4 g crude drug/kg/d. The concentration of the test solution is 2 g crude drug/ml, converting into the dosage of mice based on volume is (1.4/2)*1=0.7 ml/kg/d, and thus the high, medium and low doses of the three traditional Chinese medicine compositions are 1.4 ml/kg/d, 0.7 ml/kg/d, and 0.35 ml/kg/d (respectively corresponding to twice, equivalent and ½ fold of the clinical dose for adult).

2.1.2 Compound cyclophosphamide tablet: the clinical recommended dose for adult is 175 mg/60 kg/d. Converted according to the test body surface area in terms of human and animal, the dosage of mice is 11 times the dosage of human, and the administration dose of mice is (175/60)×11=32 mg/kg/d.

2.2 Culture of the human lung adenocarcinoma cell line (A549). Cells were cultured in complete medium (DMEM medium+10% fetal calf serum, pH 7.2), placed in 37° C. 5% $CO_2$ incubator, replaced medium daily. When cells were grown to 80-90% fusion rate, digested with 0.25% trypsin and were passaged after centrifugation. Until cells were grown to a certain amount, diluted into tumor cells suspension in PBS to inject into the test animal model.

2.3 In vitro activity assay and preparation of tumor cell suspension. The selected well-growing tumor cells were digested with 0.25% trypsin and were suspended after centrifugation under sterile conditions. Cell viability was measured and counted using trypan blue staining by a fully automated cell counter. The tumor cell suspension was diluted with PBS to a concentration of $2\times10^7$ cells/ml.

2.4 Preparation of human lung cancer xenograft model by injection of A549 tumor cells. 18±2 g nude mice were selected, male and female evenly, and adaptive feeding in experimental animal centers for 7 days. Under sterile conditions, nude mice were disinfected with 75% ethanol, and 0.2 ml of human lung adenocarcinoma A549 cell suspension was subcutaneous injected into the right armpit of nude mice. After injection, the nude mice were returned to the cage, and the spirit diet and defecation of the mice were observed regularly. About 1 week after injection, the built xenograft model was confirmed by observed the grain size hard lumps grown under the skin of injection position.

2.5 Grouping and administration. 2 weeks after tumor cells injection, the nude mice with evenly lump and weight were randomly divided into 8 groups: model control group, cyclophosphamide positive control group, traditional Chinese medicine composition No. 1 with high, medium, low three dose groups, and traditional Chinese medicine composition No. 2 with high, medium, low three dose groups. 7 mice in each group were administered on the day of grouping, and the dose was 0.2 ml/10 g once a day, orally, for 3 weeks.

2.6 Observation index. The body weight and tumor volume of nude mice were measured on the day of administration. The mice were measured every 3 days. The nude mice were weighed and sacrificed three weeks later, and the tumor tissues were weighed. The average tumor weight, tumor growth inhibition rate, tumor volume relative volume, and relative tumor growth rate of each group were calculated.

Calculation Method:

Tumor volume (TV) is calculated as: $V=\frac{1}{2}\times a\times b^2$, and a and b represent the length, width and height, respectively.

Relative tumor volume (RTV) is calculated as follows: $RTV=Vt/V0$, V0 is the tumor volume obtained at grouping (i.e. d0), and Vt is the tumor volume at each measurement.

Relative tumor growth rate T/C (%) (Evaluation index of anti-tumor activity) is calculated as: T/C %=TRTV/CRTV× 100%. (TRTV: treatment group RTV; CRTV: negative control group RTV).

2.7 Statistical processing of experimental data. After the Excel table was completed, the SPSS13.0 statistical software package was used for analysis, and the measurement data was referred to as $\overline{X}\pm s$ the t test was used for comparison between the two groups. One-way analysis of variance was used for comparison between groups, and $P<0.05$ was considered statistically significant.

3 Test Results 3.1 A549 tumor cell count (cell concentration at injection). After the cells were centrifuged and suspended in PBS, 20 μl trypan blue dye was added after diluted 10 μl cell suspension twice, added the suspension into cell counting plate percussion uniformly, and the cell counting plate was inserted into the automatic detecting cytometer. Total cell number: $2.14\times10^7$/ml; viable cell number: $1.5\times10^7$/ml; the number of dead cells: $6.42\times10^6$/ml; cell viability: 95.04%.

3.2 Effect of the tumor volume growth in nude mice model injected with human lung adenocarcinoma cell line (A549)

TABLE 1

Effect of the traditional Chinese medicine composition on the tumor volume in nude mice injected with human lung adenocarcinoma cell line (A549). ($\overline{X} \pm s$, n = 7)

| Group | dose | before administration | administration on Day 4 | administration on Day 8 |
|---|---|---|---|---|
| Model control | — | 11.59 ± 3.49 | 44.04 ± 16.99 | 123.95 ± 53.48 |
| Compound cyclophosphamide tablet | 32 mg · kg−1 | 12.42 ± 3.83 | 32.00 ± 11.08 | 106.33 ± 42.09 |
| traditional Chinese medicine composition No. 1 with high dose | 1.4 ml · kg−1 | 10.05 ± 4.65 | 24.32 ± 7.94* | 55.30 ± 19.01** |
| traditional Chinese medicine composition No. 1 with medium dose | 0.7 ml · kg−1 | 7.72 ± 3.80 | 24.53 ± 13.02* | 46.86 ± 38.68** |
| traditional Chinese medicine composition No. 1 with low dose | 0.35 ml · kg−1 | 8.10 ± 5.04 | 36.16 ± 17.79 | 78.73 ± 43.13* |
| traditional Chinese medicine composition No. 2 with high dose | 1.4 ml · kg−1 | 10.92 ± 7.32 | 35.30 ± 12.88 | 81.31 ± 38.60* |
| traditional Chinese medicine composition No. 2 with medium dose | 0.7 ml · kg−1 | 10.59 ± 4.43 | 19.91 ± 10.41** | 41.27 ± 22.86** |
| traditional Chinese medicine composition No. 2 with low dose | 0.35 ml · kg−1 | 10.34 ± 6.12 | 32.52 ± 8.87 | 59.09 ± 27.36** |

TABLE 1-continued

Effect of the traditional Chinese medicine composition on the tumor volume in nude mice injected with human lung adenocarcinoma cell line (A549). ($\overline{X} \pm s$, n = 7)

| Group | dose | administration on Day 12 | administration on Day 16 | administration on Day 20 |
|---|---|---|---|---|
| Model control | — | 206.57 ± 83.50 | 416.03 ± 98.29 | 792.08 ± 269.58 |
| Compound cyclophosphamide tablet | 32 mg · kg-1 | 187.94 ± 58.35 | 326.93 ± 128.45 | 455.04 ± 157.54** |
| traditional Chinese medicine composition No. 1 with high dose | 1.4 ml · kg-1 | 114.42 ± 73.39** | 208.35 ± 166.96** | 339.98 ± 226.46** |
| traditional Chinese medicine composition No. 1 with medium dose | 0.7 ml · kg-1 | 71.99 ± 51.03** | 159.24 ± 150.40** | 280.06 ± 210.39** |
| traditional Chinese medicine composition No. 1 with low dose | 0.35 ml · kg-1 | 87.82 ± 31.24** | 202.63 ± 111.31** | 382.26 ± 216.29** |
| traditional Chinese medicine composition No. 2 with high dose | 1.4 ml · kg-1 | 118.16 ± 70.50** | 255.01 ± 161.66* | 398.81 ± 280.86** |
| traditional Chinese medicine composition No. 2 with medium dose | 0.7 ml · kg-1 | 64.68 ± 43.43** | 107.22 ± 92.69** | 203.15 ± 159.32** |
| traditional Chinese medicine composition No. 2 with low dose | 0.35 ml · kg-1 | 87.82 ± 31.24** | 173.10 ± 62.49** | 317.92 ± 118.75** |

Compared with the model control group, *P < 0.05, **P < 0.01

The results showed that, from the second day of administration, the tumor volume of the two traditional Chinese medicine composition groups were all decreased compared with the tumor volume of the model control group. The tumor volume of the two traditional Chinese medicine composition groups were significantly decreased compared with the tumor volume of the model control group after the 8-20 day of administration (P<0.01, P<0.05), where the tumor volume of the traditional Chinese medicine composition No. 2 with medium dose group at the 5 detection time from day 4 to 20 of administration were different (P<0.01) compared with the tumor volume of the model control group and also the most significant from the data.

3.3 Effect of the relative tumor volume (RTV) and the relative tumor growth rate in nude mice model injected with human lung adenocarcinoma cell line (A549).

TABLE 2

Effect of the traditional Chinese medicine composition on the relative tumor volume (RTV) and relative tumor growth rate (T/C %) in nude mice injected with human lung adenocarcinoma cell line (A549). ($\overline{X} \pm s$, n = 7)

| Group | dose | administration on Day 4 | | administration on Day 8 | |
|---|---|---|---|---|---|
| | | RTV | T/C % | RTV | T/C % |
| Model control | — | 3.85 ± 1.62 | — | 10.98 ± 5.37 | — |
| Compound cyclophosphamide tablet | 32 mg · kg-1 | 2.81 ± 1.60 | 72.99 | 9.00 ± 4.22 | 81.97 |
| traditional Chinese medicine composition No. 1 with high dose | 1.4 ml · kg-1 | 2.84 ± 1.55 | 73.77 | 6.08 ± 2.14 | 55.37 |
| traditional Chinese medicine composition No. 1 with medium dose | 0.7 ml · kg-1 | 4.24 ± 4.64 | 110.13 | 9.98 ± 16.51 | 90.89 |
| traditional Chinese medicine composition No. 1 with low dose | 0.35 ml · kg-1 | 5.14 ± 2.40 | 133.51 | 11.33 ± 5.91 | 103.19 |

TABLE 2-continued

Effect of the traditional Chinese medicine composition on the relative tumor volume (RTV) and relative tumor growth rate (T/C %) in nude mice injected with human lung adenocarcinoma cell line (A549). ($\bar{X} \pm s$, n = 7)

| | | | | | |
|---|---|---|---|---|---|
| traditional Chinese medicine composition No. 2 with high dose | 1.4 ml · kg−1 | 4.17 ± 2.12 | 108.31 | 9.16 ± 4.67 | 83.42 |
| traditional Chinese medicine composition No. 2 with medium dose | 0.7 ml · kg−1 | 2.21 ± 1.41 | 57.40 | 4.20 ± 2.02 | 38.25 |
| traditional Chinese medicine composition No. 2 with low dose | 0.35 ml · kg−1 | 5.10 ± 4.62 | 132.47 | 8.54 ± 6.37 | 77.78 |

| | | administration on Day 12 | | administration on Day 16 | |
|---|---|---|---|---|---|
| Group | dose | RTV | T/C % | RTV | T/C % |
| Model control | — | 18.72 ± 8.73 | — | 37.53 ± 11.79 | — |
| Compound cyclophosphamide tablet | 32 mg · kg−1 | 16.35 ± 7.56 | 87.34 | 28.51 ± 16.56 | 75.97 |
| traditional Chinese medicine composition No. 1 with high dose | 1.4 ml · kg−1 | 11.55 ± 6.54 | 63.46 | 18.68 ± 8.79 | 49.77 |
| traditional Chinese medicine composition No. 1 with medium dose | 0.7 ml · kg−1 | 14.29 ± 21.62 | 78.52 | 21.14 ± 24.65 | 56.33 |
| traditional Chinese medicine composition No. 1 with low dose | 0.35 ml · kg−1 | 16.11 ± 9.25 | 86.06 | 28.25 ± 14.24 | 61.95 |
| traditional Chinese medicine composition No. 2 with high dose | 1.4 ml · kg−1 | 12.73 ± 6.63 | 69.95 | 29.61 ± 19.66 | 78.90 |
| traditional Chinese medicine composition No. 2 with medium dose | 0.7 ml · kg−1 | 6.56 ± 4.00 | 35.04 | 10.78 ± 9.00 | 28.72 |
| traditional Chinese medicine composition No. 2 with low dose | 0.35 ml · kg−1 | 12.43 ± 9.03 | 65.92 | 23.05 ± 14.07 | 61.42 |

| | | administration on Day 20 | |
|---|---|---|---|
| Group | dose | RTV | T/C % |
| Model control | — | 70.25 ± 26.43 | — |
| Compound cyclophosphamide tablet | 32 mg · kg−1 | 40.66 ± 22.80 | 57.88 |
| traditional Chinese medicine composition No. 1 with high dose | 1.4 ml · kg−1 | 31.73 ± 12.50 | 45.01 |
| traditional Chinese medicine composition No. 1 with medium dose | 0.7 ml · kg−1 | 56.15 ± 84.70 | 79.93 |
| traditional Chinese medicine composition No. 1 with low dose | 0.35 ml · kg−1 | 52.74 ± 28.24 | 75.07 |
| traditional Chinese medicine composition No. 2 with high dose | 1.4 ml · kg−1 | 45.27 ± 29.78 | 64.44 |
| traditional Chinese medicine composition No. 2 with medium dose | 0.7 ml · kg−1 | 20.60 ± 15.79* | 29.32 |

TABLE 2-continued

Effect of the traditional Chinese medicine composition on the
relative tumor volume (RTV) and relative tumor growth rate (T/C %) in nude
mice injected with human lung adenocarcinoma cell line (A549). ($\overline{X} \pm s$, n = 7)

| | | | |
|---|---|---|---|
| traditional Chinese medicine composition No. 2 with low dose | 0.35 ml · kg−1 | 38.76 ± 17.94 | 55.17 |

Compared with the model control group, *P < 0.05, **P < 0.01

The results showed that the RTV of the traditional Chinese medicine composition No. 2 with medium dose group was different compared with the RTV of the model control group (P<0.05), and the rest of the administration groups and model groups has no differences. Compared with the model control group, the T/C % of the traditional Chinese medicine composition No. 1 with high dose group and the traditional Chinese medicine composition No. 2 with medium dose group were 28-70%, and the T/C % of the rest of the administration groups were between 50-90%.

3.4 Effect of the tumor weight in nude mice model injected with human lung adenocarcinoma cell line (A549).

TABLE 3

Effect of the traditional Chinese medicine composition on the
tumor weight in nude mice injected with human lung
adenocarcinoma cell line (A549). ($\overline{X} \pm s$, n = 7)

| Group | dose | tumor weight |
|---|---|---|
| Model control | — | 0.610 ± 0.058 |
| Compound cyclophosphamide tablet | 32 mg · kg−1 | 0.381 ± 0.133** |
| traditional Chinese medicine composition No. 1 with high dose | 1.4 ml · kg−1 | 0.210 ± 0.114** |
| traditional Chinese medicine composition No. 1 with medium dose | 0.7 ml · kg−1 | 0.187 ± 0.138** |
| traditional Chinese medicine composition No. 1 with low dose | 0.35 ml · kg−1 | 0.306 ± 0.191** |
| traditional Chinese medicine composition No. 2 with high dose | 1.4 ml · kg−1 | 0.300 ± 0.250** |
| traditional Chinese medicine composition No. 2 with medium dose | 0.7 ml · kg−1 | 0.125 ± 0.108** |
| traditional Chinese medicine composition No. 2 with low dose | 0.35 ml · kg−1 | 0.255 ± 0.085** |

Compared with the model control group, *P < 0.05, **P < 0.01

Each tumor weight of the administration groups had difference from the tumor weight of the model control group (P<0.01), and the traditional Chinese medicine composition No. 2 with medium dose group had the smallest tumor lump.

4. Summary

The traditional Chinese medicine composition of the present disclosure has inhibition on the tumor growth of the nude mice injected with human lung adenocarcinoma cell line (A549). Both two the traditional Chinese medicine composition can decrease the tumor volume, RTV, T/C %, and tumor weight of nude mice. The efficacy from high to low was the traditional Chinese medicine composition No. 2> the traditional Chinese medicine composition No. 1> compound cyclophosphamide tablet.

The foregoing is only preferred embodiments of the present disclosure, they are used to illustrate the application of the traditional Chinese medicine composition for treating tumor, and not to limit the scope of the present disclosure. In the scope of the present disclosure described in the claims and their equivalents.

What is claimed is:

1. A medicinal composition for treating tumors, wherein the medicinal composition is prepared by raw materials with weight percentage as follows:
    Sophora flavescens 3%-12%, wild Chrysanthemum flower 5%-15%, honeysuckle 2%-12%, mint 5%-15%, Poria cocos 5%-15%, Atractylodes lancea 10%-20%, cinnamon 0.5%-3%, clove 0.5%-3%, Astragalus 3%-12%, Ganoderma lucidum 5%-15%, Ligusticum striatum 10%-20%, Aucklandia root 5%-12%, and Radix glycyrrhizae 2%-10%;
    wherein a dosage form of the medicinal composition is a pill, a capsule, a tablet, a gel, or a film.

2. A preparation method of the medicinal composition according to claim 1, wherein the preparation method comprises the following steps:
    step (1), weighing the raw materials-according to the weight percentage, respectively crushing and sieving the crushed raw materials and mixing uniformly to obtain a powder;
    step (2), preparing ethanol solution, infiltrating the powder prepared from step (1) with the ethanol solution, and adding the infiltrated powder into a percolator;
    step (3), adding more of the ethanol solution to the percolator from step (2) to soak the infiltrated powder, after soaking, obtaining alcohol percolate by performing percolation, obtaining drug residues after percolation, and obtaining a medicinal compound powder A by concentrating and drying the obtained alcohol percolate;
    step (4), decocting the drug residues obtained from step (3) with water, obtaining filtrate of the decocted drug residues by filtrating, and obtaining a medicinal compound powder B by concentrating and drying the obtained filtrate of the decocted drug residues;
    step (5), uniformly mixing the medicinal compound powder A obtained from step (3) and the medicinal compound powder B obtained from step (4) to obtain the medicinal composition.

3. The preparation method of the medicinal composition according to claim 2, wherein
    in step (1), the size of the crushed raw materials is 10-100 mesh;
    in step (2) and step (3), the concentration of the ethanol solution is 40-95%;

in step (2), the infiltrating time is 10-48 hours;
in step (3), the soaking time is 2-48 hours;
in step (4), the amount of water is 2-10 times of the drug residues, and the decoction is 1-3 times, each time for 0.5-2 hours.

4. A preparation method of the medicinal composition according to claim 1, wherein the preparation method comprises the following steps:
step (1), weighing the raw materials according to the weight percentage, crushing the raw materials to 10-100 mesh, sieving the crushed raw materials, and uniformly mixing to obtain a uniformly mixed powder;
step (2), preparing an ethanol solution with a concentration of 40-95% for use; infiltrating the uniformly mixed powder with the ethanol solution for 10-48 hours, and adding the infiltrated powder into a percolator and gently pressing and flattening the infiltrated powder;
step (3), adding the ethanol solution into the percolator from step (2) till beyond the surface of the raw materials 1-2 cm, soaking for a preset time, obtaining alcohol percolate by performing percolation, reserving drug residues for use, and obtaining a medicinal compound powder A by concentrating under pressure and drying the obtained alcohol percolate;
step (4), adding 2-10 times of the drug residues amount of water to the drug residues, decocting for 0.5-2 hours, centrifuging and filtering, obtaining a medicinal compound powder B by concentrating and drying under reduced pressure, and obtaining the medicinal composition by uniformly mixing the medicinal compound powder A and the medicinal compound powder B.

5. The preparation method of the medicinal composition according to claim 4, wherein
in step (1), the size of the crushed raw materials is 20-40 mesh;
in step (2) and step (3), the concentration of the ethanol solution is 60-80%;
in step (2), infiltrating the uniformly mixed powder for 18-30 hours;
in step (3), the soaking time is 2-48 hours.

6. A preparation method of the medicinal composition according to claim 1, wherein the preparation method comprises the following steps:
step (1), weighing first medicinal materials including *Ligusticum striatum, Atractylodes lancea, Aucklandia* root, clove, cinnamon, and mint according to the weight percentage, extracting volatile oil and obtaining decocted residues by decocting the first medicinal materials with water, processing the extracted volatile oil with cyclodextrin to obtain a volatile oil cyclodextrin inclusion complex, and filtering the decocted residues to obtain first filtrate and drug residues for later use;
step (2), mixing the drug residues obtained from step (1) with weighed second medicinal materials including *Poria cocos, Astragalus*, wild *Chrysanthemum* flower, *Ganoderma lucidum*, honeysuckle, *Sophora flavescens*, and *Radix glycyrrhizae*, according to the weight percentage, decocting the mixed drug residues and the second medicinal materials with water and then filtrating to obtain second filtrate, and combining the second filtrate with the first filtrate obtained from step (1) to obtain medicinal mixed solution;
step (3), concentrating the medicinal mixed solution obtained from step (2) to paste, adding ethanol to the paste to make the paste precipitating in ethanol, and obtaining a mixed alcohol solution by filtration;
step (4), concentrating and drying the mixed alcohol solution obtained from step (3), adding the volatile oil cyclodextrin inclusion complex from step (1) to obtain the medicinal composition.

7. The preparation method of the medicinal composition according to claim 6, wherein
in step (1), the amount of water used in decocting process is 4-15 times of the amount of the first medicinal materials, the extraction time is 2-12 hours, the volatile oil is processed with a cyclodextrin inclusion process below 40° C., and a time of the cyclodextrin inclusion process is 1-10 hours;
step (2) further comprises: mixing the drug residues obtained from step (1) with the weighed second medicinal materials including *Poria cocos, Astragalus*, wild *Chrysanthemum* flower, *Ganoderma lucidum*, honeysuckle, *Sophora flavescens*, and *Radix glycyrrhizae*, according to the weight percentage, adding 10-15 times of the amount of the second medicinal materials of water and decocting for 2-5 times, each time for 1-2 hours, and then filtrating to obtain the second filtrate, and mixing the second filtrate with the first filtrate obtained from step (1) to obtain the medicinal mixed solution;
step (3) further comprises: concentrating the medicinal mixed solution obtained from step (2) by water bath to the paste with a density of 1.06-1.08 q/cm$^3$, adding ethanol to make the ethanol content up to 60%, standing still for 12-72 hours, and filtrating to obtain the mixed alcohol solution.

8. A preparation method of the medicinal composition according to claim 1, wherein the preparation method comprises the following steps:
step (1), weighing first medicinal materials including *Ligusticum striatum, Atractylodes lancea, Aucklandia* root, clove, cinnamon, and mint according to the weight percentage, extracting volatile oil and obtaining decocted residues by decocting the first medicinal materials with water, processing the extracted volatile oil with cyclodextrin to obtain a volatile oil cyclodextrin inclusion complex, and filtering the decocted residues to obtain first filtrate and drug residues for later use;
step (2), mixing the drug residues with weighed second medicinal materials including *Poria cocos, Astragalus*, wild *Chrysanthemum* flower, *Ganoderma lucidum*, honeysuckle, *Sophora flavescens*, and *Radix glycyrrhizae*, according to the weight percentage, decocting the mixed drug residues and the second medicinal materials with water and then filtrating to obtain second filtrate, and combining the second filtrate with the first filtrate obtained from step (1) to obtain a medicinal mixed solution;
step (3), concentrating the medicinal mixed solution to paste by water bath, adding ethanol to the paste to make the paste precipitating in ethanol, adding ethanol to make the ethanol content up to 50-80% to obtain a medicinal mixed alcohol solution;
step (4), concentrating the medicinal mixed alcohol solution under reduced pressure, drying, adding the volatile oil cyclodextrin inclusion complex to obtain the medicinal composition.

9. The preparation method of the medicinal composition according to claim 8, wherein
in step (1), the amount of water used in decocting process is 4-15 times of the amount of the first medicinal materials, the extraction time is 2-12 hours, the volatile oil is processed with cyclodextrin below 40° C., and a time of the cyclodextrin inclusion process is 1-10 hours.

10. The preparation method of the medicinal composition according to claim 8, wherein
the step (2) further comprises: mixing the drug residues obtained from step (1) with the weighed second medicinal materials including *Poria cocos, Astragalus*, wild *Chrysanthemum* flower, *Ganoderma lucidum*, honeysuckle, *Sophora flavescens*, and *Radix glycyrrhizae*, according to the weight percentage, adding 10-15 times of the amount of the second medicinal materials of water and decocting for 2-5 times, each time for 1-2 hours, and then filtrating to obtain the second filtrate, and mixing the second filtrate with the first filtrate obtained from step (1) to obtain the medicinal mixed solution.

11. The preparation method of the medicinal composition according to claim 8, wherein
the step (3) further comprises: concentrating the medicinal mixed solution by water bath to the paste with a density of 1.06-1.08 q/cm³, adding ethanol to make the ethanol content up to 60%, and standing still for 12 hours or more to obtain the medicinal mixed alcohol solution.

12. A preparation method of the medicinal composition according to claim 1, wherein the preparation method comprises the following steps:
step (1), weighing each of the raw materials according to the weight percentage, and mixing uniformly;
step (2), adding ethanol solution into the uniformly mixed raw materials from step (1), obtaining extract solution by heating and refluxing for 1-2 hours, performing the above part of step (2) for 1-4 times, merging the extract solution of each refluxing process, recovering the ethanol under reduced pressure, and concentrating and drying to obtain the medicinal composition.

13. A preparation method of the medicinal composition according to claim 1, wherein the preparation method comprises the following steps:
step (1), weighing the raw materials according to the weight percentage, and mixing uniformly;
step (2), preparing 40-80% ethanol solution for use, adding the uniformly mixed raw materials into the prepared ethanol solution, obtaining extract solution by heating and refluxing for 1-2 hours, performing the above part of step (2) for 1-4 times, merging the extract solution, recovering the ethanol under reduced pressure, and concentrating and drying to obtain the medicinal composition.

14. A method for treating tumors, wherein the medicinal composition according to claim 1 is administered to a subject in need thereof.

15. The medicinal composition according to claim 1, wherein the medicinal composition is used for treating a tumor.

16. The medicinal composition according to claim 1, wherein the medicinal composition is prepared by raw materials with weight percentage as follows:
*Sophora flavescens* 5%-10%, wild *Chrysanthemum* flower 5%-10%, honeysuckle 3%-8%, mint 5%-10%, *Poria cocos* 5%-10%, *Atractylodes lancea* 12%-20%, cinnamon 0.5%-3%, clove 0.5%-3%, *Astragalus* 5%-10%, *Ganoderma lucidum* 5%-10%, *Ligusticum striatum* 11%-15%, *Aucklandia* root 8%-12%, and *Radix glycyrrhizae* 3%-8%.

17. The medicinal composition according to claim 16, wherein the medicinal composition is prepared by raw materials with weight percentage as follows:
*Sophora flavescens* 6%-10%, wild *Chrysanthemum* flower 6%-9%, honeysuckle 3%-6%, mint 6%-9%, *Poria cocos* 6%-9%, *Atractylodes lancea* 15%-18%, cinnamon 1%-3%, clove 0.5%-1.5%, *Astragalus* 6%-10%, *Ganoderma lucidum* 6%-10%, *Ligusticum striatum* 12%-15%, *Aucklandia* root 8%-11%, and *Radix glycyrrhizae* 3%-6%.

18. The medicinal composition according to claim 17, wherein the medicinal composition is prepared by raw materials with weight percentage as follows:
*Sophora flavescens* 8%, wild *Chrysanthemum* flower 9%, honeysuckle 4%, mint 6%, *Poria cocos* 6%, *Atractylodes lancea* 17%, cinnamon 2%, clove 1%, *Astragalus* 8%, *Ganoderma lucidum* 10%, *Ligusticum striatum* 13%, *Aucklandia* root 9%, and *Radix glycyrrhizae* 7%.

19. The medicinal composition according to claim 17, wherein the medicinal composition is prepared by raw materials with weight percentage as follows:
*Sophora flavescens* 7%, wild *Chrysanthemum* flower 7%, honeysuckle 6%, mint 8%, *Poria cocos* 8%, *Atractylodes lancea* 15%, cinnamon 2%, clove 1.5%, *Astragalus* 7%, *Ganoderma lucidum* 8%, *Ligusticum striatum* 15%, *Aucklandia* root 10%, and *Radix glycyrrhizae* 5.5%.

20. The medicinal composition according to claim 17, wherein the medicinal composition is prepared by raw materials with weight percentage as follows:
*Sophora flavescens* 8%, wild *Chrysanthemum* flower 7%, honeysuckle 5%, mint 6%, *Poria cocos* 9%, *Atractylodes lancea* 18%, cinnamon 1.5%, clove 0.5%, *Astragalus* 6%, *Ganoderma lucidum* 9%, *Ligusticum striatum* 16%, *Aucklandia* root 9%, and *Radix glycyrrhizae* 5%.

21. The medicinal composition according to claim 17, wherein the medicinal composition is prepared by raw materials with weight percentage as follows:
*Sophora flavescens* 6%, wild *Chrysanthemum* flower 9%, honeysuckle 8%, mint 5%, *Poria cocos* 9%, *Atractylodes lancea* 19%, cinnamon 1%, clove 1%, *Astragalus* 6%, *Ganoderma lucidum* 15%, *Ligusticum striatum* 11%, *Aucklandia* root 9%, and *Radix glycyrrhizae* 10%.

22. The medicinal composition according to claim 17, wherein the medicinal composition is prepared by raw materials with weight percentage as follows:
*Sophora flavescens* 9%, wild *Chrysanthemum* flower 8%, honeysuckle 3%, mint 9%, *Poria cocos* 8%, *Atractylodes lancea* 16.5%, cinnamon 1%, clove 1%, *Astragalus* 9%, *Ganoderma lucidum* 9%, *Ligusticum striatum* 13.5%, *Aucklandia* root 10%, and *Radix glycyrrhizae* 3%.

23. The preparation method of the medicinal composition according to claim 3, wherein
in step (1), the size of the crushed raw materials is 20-40 mesh.

24. The preparation method of the medicinal composition according to claim 3, wherein
in step (2) and step (3), the concentration of the ethanol solution is 60-80%.

25. The preparation method of the medicinal composition according to claim 3, wherein
in step (2), the infiltrating time is 18-30 hours.

26. The preparation method of the medicinal composition according to claim 12, wherein
in step (2), the concentration of the ethanol solution is 40-80%.

27. A preparation method of a medicinal composition, wherein the preparation method comprises the following steps:
step (1), weighing raw materials with weight percentage including *Sophora flavescens* 3%-12%, wild *Chrysanthemum* flower 5%-15%, honeysuckle 2%-12%, mint 5%-15%, *Poria cocos* 5%-15%, *Atractylodes lancea* 10%-20%, cinnamon 0.5%-3%, clove 0.5%-3%, *Astragalus* 3%-12%, *Ganoderma lucidum* 5%-15%, *Ligusticum striatum* 10%-20%, *Aucklandia* root 5%-12%, and *Radix glycyrrhizae* 2%-10%, respectively crushing and sieving the crushed raw materials and mixing uniformly to obtain a powder;
step (2), preparing ethanol solution, infiltrating the powder prepared from step (1) with the ethanol solution, and adding the infiltrated powder into a percolator;
step (3), adding more of the ethanol solution to the percolator from step (2) to soak the infiltrated powder, after soaking, obtaining alcohol percolate by performing percolation, obtaining drug residues after percolation, and obtaining a medicinal compound powder A by concentrating and drying the obtained alcohol percolate;
step (4), decocting the drug residues obtained from step (3) with water, obtaining filtrate of the decocted drug residues by filtrating, and obtaining a medicinal compound powder B by concentrating and drying the obtained filtrate of the decocted drug residues;
step (5), uniformly mixing the medicinal compound powder A obtained from step (3) and the medicinal compound powder B obtained from step (4) to obtain the medicinal composition.

28. The preparation method of the medicinal composition according to claim 27, wherein
in step (1), the size of the crushed raw materials is 10-100 mesh;
in step (2) and step (3), the concentration of the ethanol solution is 40-95%;
in step (2), the infiltrating time is 10-48 hours;
in step (3), the soaking time is 2-48 hours;
in step (4), the amount of water is 2-10 times of the drug residues, and the decoction is 1-3 times, each time for 0.5-2 hours.

29. The preparation method of the medicinal composition according to claim 28, wherein
in step (1), the size of the crushed raw materials is 20-40 mesh;
in step (2) and step (3), the concentration of the ethanol solution is 60-80%;
in step (2), the infiltrating time is 18-30 hours.

30. A preparation method of a medicinal composition, wherein the preparation method comprises the following steps:
step (1), weighing first medicinal materials with weight percentage including *Ligusticum striatum* 10%-20%, *Atractylodes lancea* 10%-20%, *Aucklandia* root 5%-12%, clove 0.5%-3%, cinnamon 0.5%-3%, and mint 5%-15%, extracting volatile oil and obtaining decocted residues by decocting the first medicinal materials with water, processing the extracted volatile oil with cyclodextrin to obtain a volatile oil cyclodextrin inclusion complex, and filtrating the decocted residues to obtain first filtrate and drug residues for later use;
step (2), mixing the drug residues obtained from step (1) with second medicinal materials with weight percentage including *Poria cocos* 5%-15%, *Astragalus* 3%-12%, wild *Chrysanthemum* flower 5%-15%, *Ganoderma lucidum* 5%-15%, honeysuckle 2%-12%, *Sophora flavescens* 3%-12%, and *Radix glycyrrhizae* 2%-10%, decocting the mixed drug residues and the second medicinal materials with water and then filtrating to obtain second filtrate, and combining the second filtrate with the first filtrate obtained from step (1) to obtain a medicinal mixed solution;
step (3), concentrating the medicinal mixed solution obtained from step (2) to paste, adding ethanol to the paste to make the paste precipitating in ethanol, and obtaining a mixed alcohol solution by filtration;
step (4), concentrating and drying the mixed alcohol solution obtained from step (3), adding the volatile oil cyclodextrin inclusion complex from step (1) to obtain the medicinal composition.

31. The preparation method of the medicinal composition according to claim 30, wherein
in step (1), the amount of water used in decocting process is 4-15 times of the amount of the first medicinal materials, the extraction time is 2-12 hours, the volatile oil is processed with a cyclodextrin inclusion process below 40° C., and a time of the cyclodextrin inclusion process is 1-10 hours;
step (2) further comprises: mixing the drug residues obtained from step (1) with the second medicinal materials including *Poria cocos, Astragalus*, wild *Chrysanthemum* flower, *Ganoderma lucidum*, honeysuckle, *Sophora flavescens*, and *Radix glycyrrhizae*, according to the weight percentage, adding 10-15 times of the amount of the second medicinal materials of water and decocting for 2-5 times, each time for 1-2 hours, and then filtrating to obtain the second filtrate, and mixing the second filtrate with the first filtrate obtained from step (1) to obtain the medicinal mixed solution;
step (3) further comprises: concentrating the medicinal mixed solution obtained from step (2) by water bath to the paste with a density of 1.06-1.08 g/cm$^3$, adding ethanol to make the ethanol content up to 60%, standing still for 12-72 hours, and filtrating to obtain the mixed alcohol solution.

32. The preparation method of the medicinal composition according to claim 30, wherein
step (2) further comprises: mixing the drug residues obtained from step (1) with the second medicinal materials including *Poria cocos, Astragalus*, wild *Chrysanthemum* flower, *Ganoderma lucidum*, honeysuckle, *Sophora flavescens*, and *Radix glycyrrhizae*, according to the weight percentage, adding 10-15 times of the amount of the second medicinal materials of water and decocting for 2-5 times, each time for 1-2 hours, and then filtrating to obtain the second filtrate, and mixing the second filtrate with the first filtrate obtained from step (1) to obtain the medicinal mixed solution;
step (3) further comprises: concentrating the medicinal mixed solution obtained from step (2) by water bath to the paste with a density of 1.06-1.08 g/cm$^3$, adding ethanol to make the ethanol content up to 60%, standing still for 12-72 hours, and filtrating to obtain the mixed alcohol solution.

* * * * *